United States Patent
Omernick et al.

(10) Patent No.: US 7,298,825 B2
(45) Date of Patent: Nov. 20, 2007

(54) PORTABLE DIGITAL DETECTOR SYSTEM

(75) Inventors: Jon C. Omernick, Wauwatosa, WI (US); Kenneth S. Kump, Waukesha, WI (US); Sabih Q. Zaman, Elm Grove, WI (US)

(73) Assignee: General Electric Co., Schenectady, NY (US)

( * ) Notice: Subject to any disclaimer, the term of this patent is extended or adjusted under 35 U.S.C. 154(b) by 36 days.

(21) Appl. No.: 11/164,438

(22) Filed: Nov. 22, 2005

(65) Prior Publication Data
US 2007/0116180 A1  May 24, 2007

(51) Int. Cl.
*H05G 1/26* (2006.01)
(52) U.S. Cl. ..................... 378/116; 378/207
(58) Field of Classification Search ........ 378/189–190, 378/115–117, 102, 207, 204, 210, 98.8
See application file for complete search history.

(56) References Cited

U.S. PATENT DOCUMENTS

| | | | |
|---|---|---|---|
| 5,265,149 A | 11/1993 | Varisco | |
| 5,687,717 A | 11/1997 | Halpern et al. | |
| 6,007,243 A | 12/1999 | Ergun et al. | |
| 6,550,964 B2 | 4/2003 | Guerit et al. | |
| 6,702,459 B2 | 3/2004 | Barnes et al. | |
| 2002/0150214 A1* | 10/2002 | Spahn | 378/189 |
| 2002/0176535 A1* | 11/2002 | Dixon et al. | 378/62 |

* cited by examiner

*Primary Examiner*—Hoon Song

(57) ABSTRACT

A detector for a portable imaging system includes a flash memory including a full set of configuration parameters and calibration files. The detector also includes a transmit and receive unit for communicating with the portable imaging system. The detector still further includes a detector controller responding to a request for identification of the detector received through the transmit and receive unit. The detector transmits calibration data and configuration data from the flash memory to the portable imaging system and boots the detector.

20 Claims, 2 Drawing Sheets

PORTABLE DIGITAL DETECTOR SYSTEM

TECHNICAL FIELD

The present invention relates generally to imaging systems and more particularly to mobile radiography.

BACKGROUND

In the hospital setting, mobile radiographic exams are performed on patients incapable of being moved or difficult to move. Also, in tertiary care medical centers, mobile radiographic exams represent a significant percentage of the radiographic exams performed.

When a portable digital detector is used in the mobile radiology (RAD) clinical environments, it is critical that the system be reliable and available to the user (i.e. maximization of uptime). Due to the harsh environment in which this type of detector is used, (detector being dropped, banged against objects, etc.) it is inevitable that the detector may need to be replaced on a clinical site. It is desirable that the time to replace the detector and return the system back to the customer be as short as possible. With current remote diagnostic capabilities, it is possible to determine which component has failed and to provide the proper part to the site.

If, however, once the detector has been replaced, a long configuration, calibration process is required, as is often the case, time for the user to receive the unit and restart patient procedures may be significantly impacted. As the cost of the system requires high productivity and low downtime, it is critical to reduce or eliminate this effort.

In addition, if any change to the detector design occurs during production it would be highly beneficial for the detector itself to include any configuration parameters that would be affected without requiring the customer to reload new software on the system prior to using the detector.

Also, if multiple detectors are available to the customer and the detector is capable of quickly switching through wireless or quick disconnect connections, the capability quickly to configure the system to work optimally with that detector may add to time saving.

The disadvantages associated with current, portable digital detectors for mobile radiography units have made it apparent that a new technique for installing detectors and configuring portable detector information would be beneficial. The present invention is directed to these ends.

SUMMARY OF THE INVENTION

In accordance with one aspect of the present invention, a detector for a portable imaging system includes a flash memory including a full set of configuration parameters and calibration files. The detector also includes a transmit and receive unit for communicating with the portable imaging system. The detector still further includes a detector controller responding to a request for identification of the detector received through the transmit and receive unit. The detector transmits calibration data and configuration data from the flash memory to the portable imaging system and boots the detector.

In accordance with another embodiment of the present invention, a method for auto-configuring an imaging system having a portable detector and an imaging computer includes installing the portable detector in the imaging system. The imaging system checks the detector for identification information and requests configuration data from the detector in response to a difference between imaging system identification information for the detector and detector identification information. Detector calibration and configuration data is then loaded from the detector to the imaging system.

This invention provides a robust system and method for quickly switching detectors after component failure or system usage and configuring the system to allow it to be returned to customer operation.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF THE DRAWINGS

For a more complete understanding of the invention, there will now be described some embodiments thereof, given by way of example, reference being made to the accompanying drawings, in which.

DETAILED DESCRIPTION

The present invention is illustrated with respect to a mobile radiology scanning system 10, particularly suited to the medical field. The present invention is, however, applicable to various other uses that may require x-ray scanning, as will be understood by one skilled in the art.

In one embodiment, the present invention describes a system including an x-ray source assembly, a controller, and a detector attached to a mobile radiographic system.

Through the device and method of the present invention, the process of installing a detector is illustrated.

Figure 1:
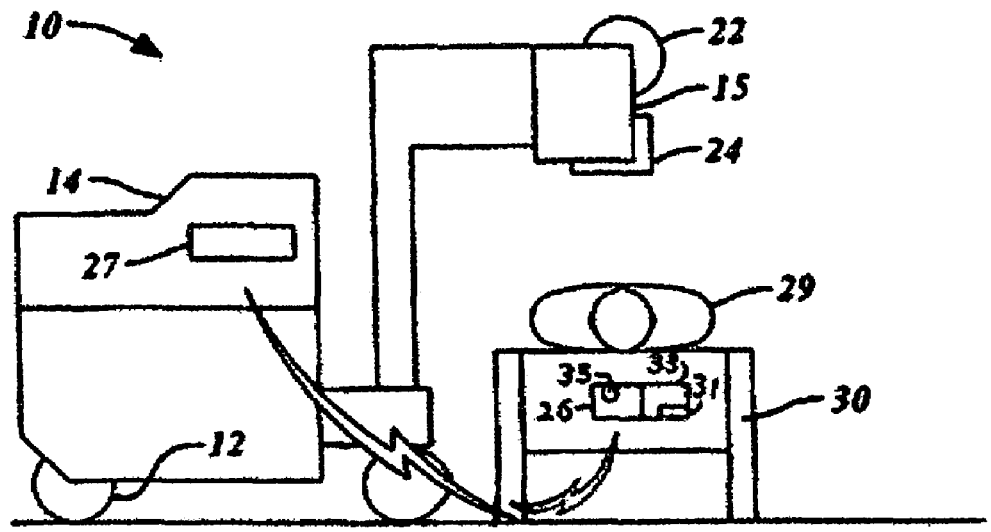
FIG. 1 is a diagram of a scanning system, in accordance with one embodiment of the present invention.
Figure 2:
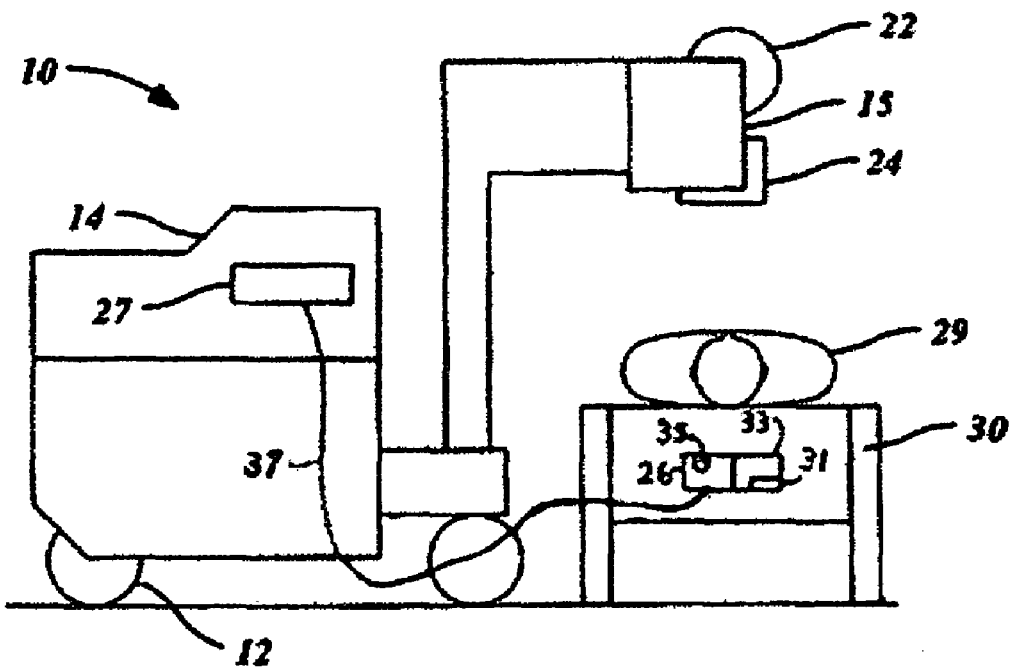
FIG. 2 is a diagram of a scanning system, in accordance with another embodiment of the present invention.
Figure 3:
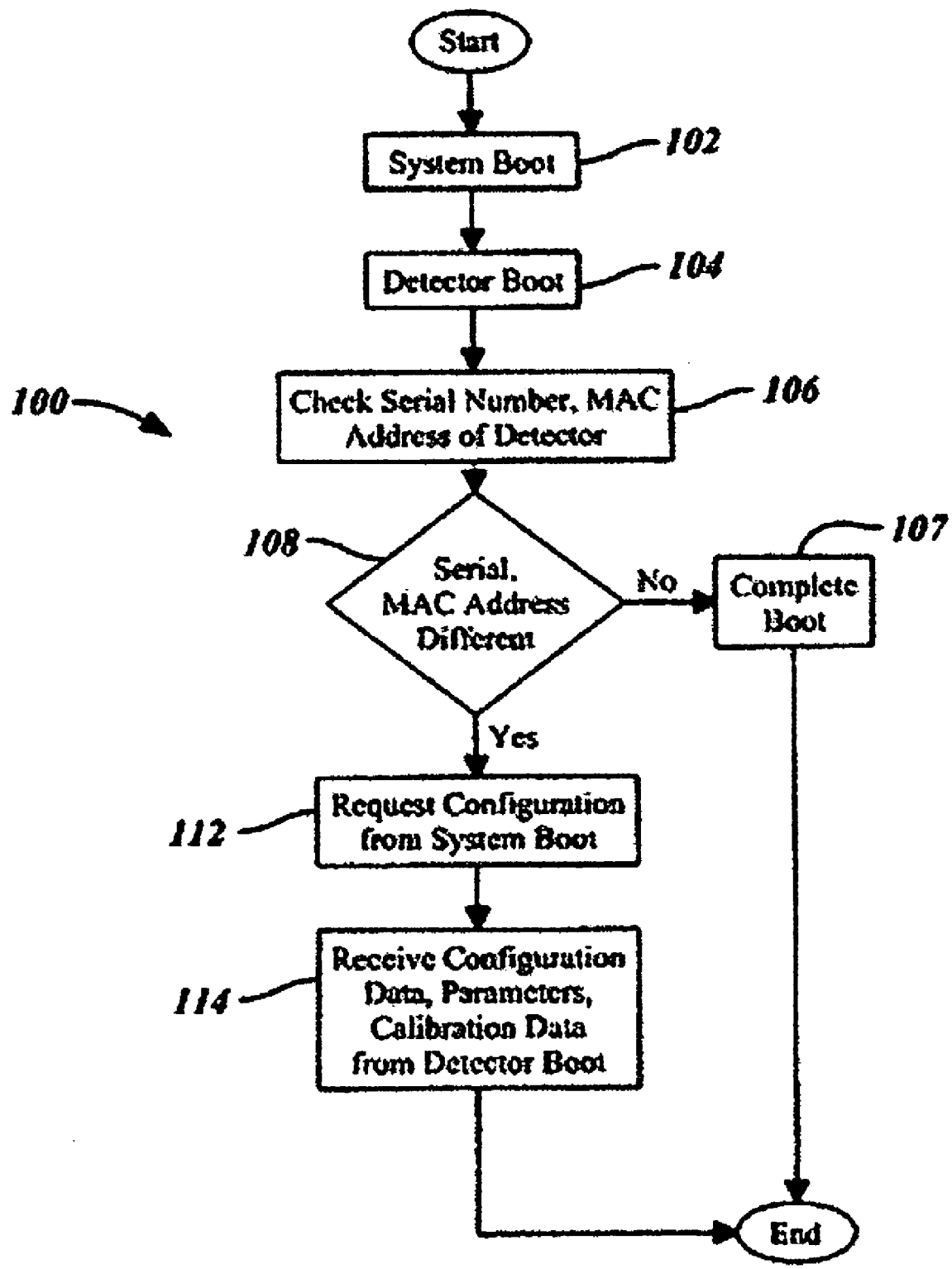
FIG. 3 is a logic flow diagram of a method for auto-configuring a portable detector, in accordance with another embodiment of the present invention.

Referring now to FIGS. 1 and 2, a mobile radiography or x-ray scanning system 10 includes a wheeled base 12, an operator console 14, and an x-ray source assembly 15. The x-ray source assembly 15 includes an x-ray tube housing 22 containing an x-ray source, the tube housing 22 having an x-ray emission aperture (not shown), and a collimator 24 attached to the tube housing 22 and aligned with the x-ray emission aperture. The scanning system 10 is embodied for scanning an object 29 to be imaged, illustrated on a table 30.

The mobile system 10 further includes a controller 27 (imaging computer) and a removeable detector 26 in communication with the controller 27.

The controller 27 includes logic checking for at least one of a serial number and MAC address from the detector. In response to at least one of the serial number and the MAC address not found in the imaging computer, the controller 27 receives data from the detector 26 configuring and calibrating the controller 27 such that the controller 27 recognizes the detector and operates with the detector 26. In other words, if the controller 27 does not include configuration data for or does not recognize the detector 26, the detector transmits information required to run that particular detector.

FIG. 1 illustrates the controller 27 communicating wirelessly with the detector 26 as the detector 26 is activated and brought in a vicinity of the controller 27. FIG. 2 illustrates the detector 26 coupled to the imaging system 10 through a wire 37.

The detector 26 attaches to the system 10, on, for example, a collimator 24. The detector 26 includes a flash memory 31, a detector controller 33, and a transmit/receive unit 35. The detector 26 is positioned to produce an image of a target array 28.

In accordance with one embodiment of the present invention, a detector platform, such as the Geode portable detector platform, includes flash memory 31, which is loaded from the vendor with a full set of configuration parameters and calibration files. This data is uploaded to the system controller 27 based on the MAC address or serial number on system boot after the detector 26 is re-connected. The data included in the flash data includes all calibration data, model information and component configuration data.

In accordance with another embodiment of the present invention, if during system operation, calibration is required either due to changes of the detector 26 or for image quality (IQ) requirements, this new calibration data will be transferred back to the detector 26 from the controller 27 for ensuring that the data on the detector 26 is refreshed.

The detector 26 includes the transmit/receive unit 35 for communicating with the controller 27. The transmit/receive unit 35 may be wireless or may include wires connecting to the controller 27 or to another part of the imaging system 10.

The detector 26 further includes the detector controller 33 receiving and processing signals from the controller 27 and controlling boot functions of the detector 26, including configuring the detector 26 for use with the particular imaging system 10.

While it is preferred that the detector 26 be affixable to the collimator housing 24, it is appreciated that the detector 26, according to the present invention, can be mounted in a variety of positions on the mobile x-ray system 10. It is further recognized that other detectors and numerous numbers thereof, in addition to a digital detector, are operative herein. These additional detectors may be optical in nature, or be based on other principles such as magnetic interactions, ultrasound, or inertial navigation.

Referring to FIG. 2, a logic flow diagram 100 of one embodiment of the operations of the present invention is illustrated.

In operation block 102, the controller or system boot activates, and in operation block 104, the detector boot activates.

In operation block 106, serial numbers and MAC addressed are checked between the system boot and the detector boot. This is conducted in either the system controller or the detector or both.

In inquiry block 108, a check is made whether the serial numbers and MAC addresses are different. For a negative response the boot completes.

Otherwise, in operation block 112 the detector requests configuration data from the system boot, or the system boot automatically updates the detector.

In operation block 114, configuration data, detector parameters, and calibration data is received in the system boot in response to system boot request or automatic detector signal.

In operation, a method for auto-configuring an imaging system having a portable detector and an imaging computer includes installing the portable detector in the imaging system. The imaging system checks the detector for identification information and requests configuration data from the detector in response to a difference between imaging system identification information for the detector and detector identification information. Detector calibration and configuration data is then loaded from the detector to the imaging system.

From the foregoing, it can be seen that there has been brought to the art a scanning system 10 and method. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

What is claimed is:

1. A detector for a portable imaging system comprising:
   a flash memory comprising a full set of calibration data and configuration data;
   a transmit and receive unit for communicating with the portable imaging system; and
   a detector controller responding to a request for identification of said detector received through said transmit and receive unit and transmitting calibration data and configuration data from said flash memory to the portable imaging system and booting the detector.

2. The system of claim 1, wherein said transmit and receive unit comprises at least one of a wireless unit or an electrical connection.

3. The system of claim 1, wherein said detector controller comprises detector serial number data.

4. The system of claim 1, wherein said detector controller comprises detector Media Access Control (MAC) address data.

5. A method for auto-configuring an imaging system having a portable detector and an imaging computer, the method comprising:
   installing the portable detector in the imaging system;
   the imaging system checking the detector for identification information;
   the imaging system requesting calibration and configuration data from the detector in response to a difference between imaging system identification information for the detector and detector identification information; and
   loading detector calibration and configuration data from the detector to the imaging system.

6. The method of claim 5, wherein said step of installing comprises the detector communicating wirelessly with the imaging system.

7. The method of claim 5 further comprising booting the detector and the imaging system as a function of said detector calibration and configuration data.

8. The method of claim 5, wherein loading detector calibration and configuration data further comprises loading detector model information.

9. The method of claim 5, further comprising in response to a calibration requirement occurring during imaging system operation, transmitting new calibration data to the detector.

10. The method of claim 5 wherein loading detector calibration and configuration data comprises uploading a full set of configuration parameters and calibration files based on at least one of a MAC address and a serial number on an image system boot after the detector is installed.

11. The method of claim 5, further comprising the imaging system completing a boot in response to consistency between said imaging system identification information for the detector and said detector identification information.

12. A portable scanning system comprising:
   an x-ray source coupled to an imaging computer and adapted to generate an x-ray exposure in response to imaging computer signals;
   a detector comprising a memory loaded with configuration parameters and calibration files, said detector communicating with said imaging computer and adapted to receive said x-ray exposure and generate therefrom a detector signal; and
   an imaging computer comprising logic checking for at least one of a serial number and MAC address from said detector, in response to said at least one of said serial number and said MAC address not found in said imaging computer, said imaging computer receiving data from said detector configuring and calibrating said imaging computer such that said imaging computer recognizes said detector and operates with said detector.

13. The system of claim 12, wherein said memory of said detector comprises a flash memory loaded.

14. The system of claim 13, wherein said flash memory is preloaded by a vendor.

15. The system of claim 12 further comprising a wireless communication system for transmitting data between said detector and said imaging computer.

16. The system of claim 12, wherein said memory further comprises detector model information.

17. The system of claim 12, wherein said imaging computer comprises logic activating in response to a calibration requirement occurring during system operation and transmitting new calibration data to said detector.

18. The system of claim 17, wherein data on said detector refreshes in response to said new calibration data.

19. The system of claim 12, wherein said detector further comprises a detector controller responding to a request for identification of said detector by sending requested identification data.

20. The system of claim 12, wherein said detector and said imaging computer boot as a function of said imaging computer recognizing said detector.

* * * * *